US012703857B2

(12) United States Patent
Ruderfer et al.

(10) Patent No.: US 12,703,857 B2
(45) **Date of Patent: *Aug. 11, 2026**

(54) METHODS OF TREATING DISEASES ASSOCIATED WITH ELEVATED URIC ACID

(71) Applicant: Protalix Ltd., Carmiel (IL)

(72) Inventors: Ilya Ruderfer, Carmiel (IL); Yakir Nataf, Kiryat Motzkin (IL); Gil Arvatz, Kfar Tavor (IL); Uri Hanania, Carmiel (IL); Tamar Ariel, Manof (IL); Shelly Rozen, Yuvalim (IL); Yael Hayon, Tel Aviv (IL); Zohar Keren, Gesher HaZiv (IL); Orit Cohen-Barak, Haifa (IL)

(73) Assignee: Protalix Ltd., Carmiel (IL)

( * ) Notice: Subject to any disclaimer, the term of this patent is extended or adjusted under 35 U.S.C. 154(b) by 167 days.

This patent is subject to a terminal disclaimer.

(21) Appl. No.: 18/429,649

(22) Filed: Feb. 1, 2024

(65) Prior Publication Data

US 2024/0263150 A1 Aug. 8, 2024

Related U.S. Application Data

(60) Provisional application No. 63/442,774, filed on Feb. 2, 2023.

(51) Int. Cl.

| | |
|---|---|
| ***C12N 9/06*** | (2006.01) |
| ***A61K 9/00*** | (2006.01) |
| ***A61K 31/519*** | (2006.01) |

(52) U.S. Cl.
CPC .......... *C12N 9/0048* (2013.01); *A61K 9/0019* (2013.01); *A61K 31/519* (2013.01)

(58) Field of Classification Search
CPC ...................... C12N 9/0048; C12Y 107/03003
See application file for complete search history.

(56) References Cited

U.S. PATENT DOCUMENTS

| | | | |
|---|---|---|---|
| 4,179,337 | A | 12/1979 | Davis et al. |
| 6,913,915 | B2 | 7/2005 | Ensor et al. |
| 8,188,224 | B2 | 5/2012 | Hartman et al. |
| 9,885,024 | B2 | 2/2018 | Williams et al. |
| 2003/0166249 | A1 | 9/2003 | Williams et al. |
| 2003/0195339 | A1 | 10/2003 | Yamasaki et al. |
| 2007/0274977 | A1 | 11/2007 | Hartman et al. |
| 2008/0159976 | A1 | 7/2008 | Hartman et al. |
| 2017/0189544 | A1 | 7/2017 | Martinez et al. |
| 2019/0309269 | A1 | 10/2019 | Hoffman et al. |
| 2022/0023394 | A1 * | 1/2022 | Botson .................... A61P 29/00 |
| 2023/0211002 | A1 | 7/2023 | Cho et al. |
| 2024/0002814 | A1 | 1/2024 | Ruderfer et al. |

FOREIGN PATENT DOCUMENTS

| | | |
|---|---|---|
| EP | 2 684 950 | 1/2014 |
| JP | 55-99189 | 7/1980 |
| JP | 2002-524053 | 8/2002 |
| JP | 2007-537992 | 12/2007 |
| JP | 2008-535500 | 9/2008 |
| JP | 2016-510601 (Part I) | 4/2016 |
| JP | 2016-510601 (Part II) | 4/2016 |
| JP | 2020-506932 | 3/2020 |
| WO | WO 00/07629 | 2/2000 |
| WO | WO 2011/107990 | 9/2011 |
| WO | WO 2011/107991 | 9/2011 |
| WO | WO 2011/107992 | 9/2011 |
| WO | WO 2016/187026 | 11/2016 |
| WO | WO 2018/169811 | 9/2018 |
| WO | WO 2019/010369 | 1/2019 |
| WO | WO 2022/097141 | 5/2022 |

OTHER PUBLICATIONS

Sarawate, Chaitanya A., et al. "Serum urate levels and gout flares: analysis from managed care data." JCR: Journal of Clinical Rheumatology 12.2 (2006): 61-65. (Year: 2006).*

Macovei, Luana Andreea, and Isabella Cristina Brujbu. "Clinical and epidemiological aspects of gout, a dysmetabolic disabling disorder." The Medical-Surgical Journal 119.1 (2015): 62-68. (Year: 2015).*

International Preliminary Report on Patentability May 19, 2023 From the International Bureau of WIPO Re. Application No. PCT IL2021/051305. (7 Pages).

International Search Report and the Written Opinion Dated Mar. 18, 2022 From the International Searching Authority Re. Application No. PCT/IL2021/051305. (14 Pages).

Baraf et al. "The Compare Head-to-Head, Randomized Controlled Trial of SEL-212 (Pegadricase Plus Rapamycin-Containing Nanoparticle, ImmTOR™) Versus Pegloticase for Refractory Gout", Rheumatology, p. 1-10, Advance Access Publication Jul. 14, 2023.

Baraf et al. "Tophus Burden Reduction With Peglioticase: Results From Phase 3 Randomized Trials and Open-Label Extension in Patients With Chronic Gout Refractory to Conventional Therapy", Arthritis Research & Therapy, 15(5): R137-1-R137-11, Published Online Sep. 26, 2013.

Botson et al. "A Randomized, Placebo-Controlled Study of Methotrexate to Increase Response Rates in Patients With Uncontrolled Gout Receiving Pegloticase: Primary Efficacy and Safety Findings", Arthritis & Rheumatology, 75(2): 293-304, Published Online Dec. 16, 2022.

Chua et al. "Use of Polyethylene Glycol-Modified Uricase (PEG-Uricase) to Treat Hyperuricemia in a Patient With Non-Hodgkin Lymphoma", Annals of Internal Medicine, 109: 114-117, Jul. 15, 1988.

(Continued)

*Primary Examiner* — Robert J Yamasaki

(57) ABSTRACT

A method of treating a disease or disorder associated with excessive uric acid levels is disclosed herein. The method comprises administering to the subject by i.v. infusion an amount of a recombinant homotetrameric uricase enzyme comprising four uricase polypeptides having the amino acid sequence as set forth in SEQ ID NO: 2, wherein the polypeptides are crosslinked by polyethylene glycol (PEG) bis-aldehyde having a molecular weight of 2-3.5 kDa.

13 Claims, No Drawings

Specification includes a Sequence Listing.

(56) References Cited

OTHER PUBLICATIONS

ClinicalTrials "A Study to Evaluate the Safety, Tolerability, PK, and PD Properties of PRX-115 in Adult Volunteers With Elevated Uric Acid Levels", ClinicaTrials.gov, ID NCT05745727, 10 P., Last Update Posted Nov. 18, 2023.

Crane et al. "Biological Activities of Uric Acid in Infection Due to Enteropathogenic and Shiga-Toxigenic *Escherichia coli*", Infection and Immunity, 84(4): 976-988, Published Online Jan. 19, 2016.

Crane et al. "Pro-Inflammatory Effects of Uric Acid in the Gastrointestinal Tract", Immunological Investigations, 43(3): 255-266, Published Online Dec. 30, 2013.

D'Alessandro et al. "Trauma/Hemorrhagic Shock Instigates Aberrant Metabolic Flux Through Glycolytic Pathways, as Revealed by Preliminary 13C-Glucose Labeling Metabolomics", Journal of Translational Medicine, 13(1): 253-1-253-14, Published Online Aug. 5, 2015.

Gallego-Delgado et al. "A Surprising Role for Uric acid: The Inflammatory Malaria Response", Current Rheumatology Report, 16(2): 401-1-401-10 Feb. 2014.

Ganson et al. Control of Hyperuricemia in Subjects With Refractory Gout, and Induction of antibody Against Poly(Ethylene Glycol) (PEG), in a Phase I Trial of Subcutaneous PEGylated Urate Oxidase, Arthritis Research & Therapy, 8(1): R12-1-R12-10, Published Online Dec. 2, 2005.

Hershfield et al. "Development of PEGylated Mammalian Urate Oxidase as a Therapy for Patients With Refractory Gout", PEGylated Protein Drugs: Basic Science and Clinical Applications, p. 217-227, 2009.

Hershfield et al. "Induced and Pre-Existing Anti-Polyethylene Glycol Antibody in a Trial of Every 3-Week Dosing of Pegloticase for Refractory Gout, Including in Organ Transplant Recipients", Arthritis Research & Therapy, 16(2): R63-1-R63-11, Published Online Mar. 7, 2014.

Kool et al. "An Unexpected Role for Uric Acid as an Inducer of T Helper 2 Cell Immunity to Inhaled Antigens and Inflammatory Mediator of Allergic Asthma", Immunity, 34(4): 527-540, Apr. 22, 2011.

Koyama et al. "Cloning, Sequence Analysis, and Expression in *Escherichia coli* of the Gene Encoding the Candida Utilis Urate Oxidase (Uricase)", The Journal of Biochemistry, 120(5): 969-973, Nov. 1, 1996.

Liu et al. "Clinical and Basic Evaluation of the Prognostic Value of Uric Acid in Traumatic Brain Injury", International Journal of Medical Sciences, 15(10): 1072-1082, Published Online Jun. 23, 2018.

Matsuo et al. "Hyperuricemia in Acute Gastroenteritis Is Caused by by Decreased Urate Excretion via ABCG2", Scientific Reports, 6: 31003-1-31003-6, Aug. 30, 2016.

Nadeau-Vallee et al. "Sterile Inflammation and Pregnancy Complications: A Review", Reproduction, 152(6): R277-R292, Published Online Sep. 27, 2016.

Nyborg et al. "A Therapeutic Uricase With Reduced Immunogenicity Risk and Improved Development Properties", PLoS ONE, 11(12): e0167935-1-e0167935-23, Dec. 21, 2016.

Piancone et al. "Monosodium Urate Crystals Activate the Inflammasome in Primary Progressive Multiple Sclerosis", Frontiers in Immunology, 9: 983-1-983-12, Published Online May 4, 2018.

Richette et al. "Rasburicase for Tophaceous Gout Not Treatable With Allupurinol: An Exploratory Study", The Journal of Rheumatology, 34(10): 2093-2098, Published Online Sep. 15, 2007.

Strand et al. "Improved Health-Related Quality of Life and Physical Function in Patients With Refractory Chronic Gout Following Treatmetn With Pegloticase: Evidence From Phase III Randomized Controlled Trials", The Journal of Rheumatology, 39(7): 1450-1457, Published Online Jun. 1, 2012.

Sundy et al. "Efficacy and Tolerability of Pegloticase for the Treatment of Chronic Gout in Patients Refractory to Conventional Treatment. Two Randomized Controlled Trials", Journal of American Medicial Association, JAMA, 306(7): 711-720, Aug. 17, 2011.

Sundy et al. "Reduction of Plasma Urate Levels Following Treatment With Multiple Doses in Pegloticase (Polyethylene Glycol-Conjugated Uricase) in Patients With Treatment-Failure Gout", Arthritis & Rheumatism, 58(9): 2882-2891, Sep. 2008.

Veronese "Peptide and Protein PEGylation: A Review of Problems and Solutions", Biomaterials, 22(5): 405-417, Mar. 2001.

Zhang et al. "Anti-PEG Antibodies in the Clinic: Current Issues and Beyond PEGylation", Journal of Controlled Release, 244(Pt.B): 184-193, Dec. 28, 2016.

Notice of Reason(s) for Rejection Dated Sep. 16, 2025 From the Japan Patent Office Re. Application No. 2023-526588 and Its Translation Into English. (8 Pages).

Official Action Dated Oct. 7, 2025 from the US Patent and Trademark Office Re. U.S. Appl. No. 18/035,149. (13 pages).

Official Action Dated May 14, 2025 from the US Patent and Trademark Office Re. U.S. Appl. No. 18/035,149. (24 pages).

Najjari et al. "The Effective Control of Hyperuricemia in Cancer Patients: A New Recombinant Conjugated Variant of Urate Oxidase", Asian Pacific Journal of Cancer Prevention, 22: 627-632, Feb. 25, 2021.

Xuc ct al. "Enzymatic Asymmetric Synthesis of Chiral Amino Acids", Chemical Society Reviews, 47: 1516-1561, 2018.

Restriction Official Action Dated Feb. 3, 2025 from the US Patent and Trademark Office Re. U.S. Appl. No. 18/035,149. (11 pages).

Notice of Allowance Dated Mar. 11, 2026 from the US Patent and Trademark Office Re. U.S. Appl. No. 18/035,149. (15 pages).

Kivitz et al. "Phase 2 Dose-Finding Study in Patients With Gout Using SEL-212, a Novel PEGylated Uricase (SEL-037) Combined With Tolerogenic Nanoparticles (SEL-110)", Rheumatology & Therapy, 10(4): 825-847, Published Online Apr. 17, 2023.

* cited by examiner

METHODS OF TREATING DISEASES ASSOCIATED WITH ELEVATED URIC ACID

RELATED APPLICATION(S)

This application claims the benefit of priority under 35 USC § 119(e) of U.S. Provisional Patent Application No. 63/442,774 filed on Feb. 2, 2023, the contents of which are all incorporated by reference as if fully set forth herein in their entirety.

SEQUENCE LISTING STATEMENT

The XML file, entitled 98986SequenceListing.xml, created on Jan. 31, 2024, comprising 3,539 bytes, submitted concurrently with the filing of this application is incorporated herein by reference.

FIELD AND BACKGROUND OF THE INVENTION

The present invention, in some embodiments thereof, relates to therapy, and more particularly, but not exclusively, to uricase and to uses thereof, for example, in reducing uric acid levels.

Uric acid is a product of metabolic breakdown of purine nucleotides. High blood concentrations of uric acid (hyperuricemia) can lead to gout and/or kidney stones, and high uric acid levels are associated with other medical conditions, including hemorrhagic shock [D'Alessandro et al., *J Transl Med* 2015, 13:253], malaria [Gallego-Delgado et al., *Curr Rheumatol Rep* 2014, 16:401]; allergic asthma [Kool et al., *Immunity* 2011, 34:P527-P540]; traumatic brain injury [Liu et al., *Int J Med Sci* 2018, 15:1072-1082]; renal dysfunction and acute gastroenteritis [Matsuo et al., *Sci Rep* 2016, 6:31003]; multiple sclerosis [Piancone et al., *Front Immunol* 2018, 9:983]; inflammatory bowel disease [Crane & Mongiardo, *Immunol Invest* 2014, 43:255-266]; gastrointestinal infection [Crane et al., *Infect Immun* 2016, 84:976-988]; and sterile inflammation and pregnancy complications [Nadeau-Vallee et al., *Reproduction* 2016, 152:R277-R292].

The usual first-line treatment of gout is to treat the symptoms, e.g., using steroidal or non-steroidal anti-inflammatory drugs. Additional drugs include allopurinol and febuxostat, inhibitors of the enzyme xanthine oxidase (which generates uric acid); and probenecid, lesinurad, and benzbromarone, which inhibit reabsorption of uric acid in the kidney.

Uricase, which is also referred to in the art as urate oxidase, is an enzyme which catalyzes oxidation of uric acid (consuming $O_2$ and producing $H_2O_2$) to 5-hydroxyisourate, which is hydrolyzed to allantoin in most animals, plants and bacteria. However, uricase is absent in humans (and several other great apes and chickens), thus rendering humans particularly susceptible to high blood concentrations of uric acid.

Rasburicase (marketed as Elitek®) is a tetrameric uricase cloned from *Aspergillus flavus*; and approved for use in the U.S. and Europe for prevention and treatment of tumor lysis syndrome in subjects receiving chemotherapy for cancer. Off-label label use of rasburicase for treating gout has also been reported [*J Rheumatol* 2007, 34:2093-2098]. Rasburicase has a half-life of 6-21 hours, and must be dosed daily via intravenous infusion.

Pegloticase (marketed as Krystexxa®) is a tetrameric pig-baboon chimeric uricase which is PEGylated, and has been approved for the treatment of refractory gout. In each of the four monomers, an average of 10 of the 30 lysine residues are conjugated by a 10 kDa PEG chains.

As a protein which is not naturally present in humans, uricase is highly immunogenic. Anaphylaxis is a potential serious side effect of both rasburicase and pegloticase. Although the PEG moieties of pegloticase may reduce the immune response towards the uricase backbone, the PEG moieties themselves can serve as a target for antibodies [Zhang et al., *J Control Release* 2016, 244:184-193; Hershfield et al., *Arthritis Res Ther* 2014, 16:R63; Ganson et al., *Arthritis Res Ther* 2006, 8:R12].

During phase 3 clinical trials for pegloticase, 26% of patients experienced infusion reactions and 6.5% of patients had reactions characterized as anaphylaxis [Baraf et al., *Arthritis Res Ther* 2013, 15:R137; Strand et al., *J Rheumatol* 2012, 39: 1450-1457]. Addition of methotrexate to the pegloticase reduced immunogenicity and lowered the incidence of infusion reactions [Botson et al, Arthritis and Rheumatol., 2022, 75:293-304].

In phase 2 and 3 trials lasting up to six months, antibodies to pegloticase were detected (using different methods) at some point in more than 80% of patients; the highest titers were associated with loss of efficacy and infusion reactions [Sundy et al., *JAMA* 2011, 306:711-720; Sundy et al., *Arthritis Rheum* 2008, 58:2882-2891].

International Patent Application Publication WO 00/07629 describes uricase covalently coupled to PEG, with an average of 2 to 10 PEG strands per uricase subunit and an average PEG molecular weight of between about 5 kDa and 100 kDa.

International Patent Application Publication WO 2011/107992 describes multimeric protein structures comprising monomers of a therapeutic protein, such as TNF-α, a luteinizing hormone, an immunoglobin, a TNF-α receptor, a CTLA-4, a urate oxidase, a VEGF, a PDGF, a VEGF receptor, a PDGF receptor, an interleukin-17 or fragments thereof, the monomers being covalently linked to one another via a linking moiety.

Koyama et al. [*J Biochem* 1996, 120:969-973] describes *Candida utilis* uricase, as well as mutants thereof in which a cysteine residue is replaced by a serine residue, leading to the conclusion that Cys168 is the only one of the 4 cysteine residues therein which is involved in enzymatic activity.

Chua et al. [*Ann Intern Med* 1988, 109:114-117] describes *Arthrobacter protoformiae* uricase modified with monofunctional (methoxy-capped) PEG and reports that it did not induce antibody production over the course of a three-week period after administration.

Additional background art includes Hershfield et al. (2009) ["Development of PEGylated mammalian urate oxidase as a therapy for patients with refractory gout" In: Veronese F. M. (Eds) PEGylated Protein Drugs: Basic Science and Clinical Applications. Milestones in Drug Therapy. Birkhäuser Basel]; Nyborg et al. [*PLOS ONE* 2016, 11:00167935]; and Veronese [*Biomaterials* 2001, 22:405-417]; U.S. Pat. Nos. 4,179,337, 6,913,915, 8,188,224, and 9,885,024; U.S. Patent Application Publication Nos. 2007/0274977 and 2008/0159976; and International Patent Application Publications WO 2011/107990, WO 2011/107991, WO 2016/187026, WO 2018/010369 and WO 2019/010369.

Additional background art includes WO2022/097141 which teaches modified uricase enzymes.

SUMMARY OF THE INVENTION

According to an aspect of the present invention there is provided a method of treating a disease or disorder associated with excessive uric acid levels in a subject in need thereof, comprising administering to the subject by i.v. infusion an amount of a recombinant homotetrameric uricase enzyme comprising four uricase polypeptides having the amino acid sequence as set forth in SEQ ID NO: 2, wherein the polypeptides are crosslinked by polyethylene glycol (PEG) bis-aldehyde having a molecular weight of 2-3.5 kDa, wherein the administering is no more than once every four weeks, wherein the amount is selected from the group consisting of 1 mg per subject, 2.0 mg per subject, 3 mg per subject, 4.0 mg per subject, 8 mg per subject, 12 mg per subject, 16 mg per subject, 18.0 mg per subject, 24 mg per subject, 36 mg per subject and 48 mg per subject.

According to an aspect of the present invention there is provided a recombinant homotetrameric uricase enzyme comprising four uricase polypeptides having the amino acid sequence as set forth in SEQ ID NO: 2 for use in the treatment, by i.v. infusion no more than once every four weeks, of a disease or disorder associated with excessive uric acid levels in a subject, wherein the polypeptides are crosslinked by polyethylene glycol (PEG) bis-aldehyde having a molecular weight of 2-3.5 kDa, wherein an amount of the enzyme per treatment is selected from the group consisting of 1 mg per subject, 2.0 mg per subject, 3 mg per subject, 4.0 mg per subject, 8 mg per subject, 12 mg per subject, 16 mg per subject, 18 mg per subject 24 mg per subject, 36 mg per subject and 48 mg per subject.

According to embodiments of the invention, the recombinant homotetrameric uricase enzyme is administered once every four weeks, the amount is 1 mg per subject, 2.0 mg per subject, 3 mg per subject, 4.0 mg per subject, 8 mg per subject, 12 mg per subject, 16 mg per subject, 18 mg per subject 24 mg per subject, 36 mg per subject and 48 mg per subject.

According to embodiments of the invention, the recombinant homotetrameric uricase enzyme is administered once every six weeks, the amount is 1 mg per subject, 2.0 mg per subject, 3 mg per subject, 4.0 mg per subject, 8 mg per subject, 12 mg per subject, 16 mg per subject, 18 mg per subject 24 mg per subject, 36 mg per subject and 48 mg per subject According to embodiments of the invention, the recombinant homotetrameric uricase enzyme is administered once every eight weeks, the amount is 1 mg per subject, 2.0 mg per subject, 3 mg per subject, 4.0 mg per subject, 8 mg per subject, 12 mg per subject, 16 mg per subject, 18 mg per subject 24 mg per subject, 36 mg per subject and 48 mg per subject.

According to embodiments of the invention, the recombinant homotetrameric uricase enzyme is administered once every ten weeks, the amount is 1 mg per subject, 2.0 mg per subject, 3 mg per subject, 4.0 mg per subject, 8 mg per subject, 12 mg per subject, 16 mg per subject, 18 mg per subject 24 mg per subject, 36 mg per subject and 48 mg per subject.

According to embodiments of the invention, the recombinant homotetrameric uricase enzyme is administered once every twelve weeks, the amount is 1 mg per subject, 2.0 mg per subject, 3 mg per subject, 4.0 mg per subject, 8 mg per subject, 12 mg per subject, 16 mg per subject, 18 mg per subject 24 mg per subject, 36 mg per subject and 48 mg per subject.

According to embodiments of the invention, the polypeptides are crosslinked by polyethylene glycol (PEG) bis-aldehyde having a molecular weight of 3.4 kDa.

According to embodiments of the invention, the administering is effected over a period of about 1 hour, or about 1.5 hours, or about 2 hours or about 3 hours.

According to embodiments of the invention, the administering is effected once every four weeks.

According to embodiments of the invention, the administering is effected once every six weeks.

According to embodiments of the invention, the administering is effected once every eight weeks.

According to embodiments of the invention, the administering is effected once every ten weeks.

According to embodiments of the invention, the administering is effected once every twelve weeks.

According to embodiments of the invention, the treatment is by i.v. infusion once every four weeks.

According to embodiments of the invention, the treatment is by i.v. infusion once every six weeks.

According to embodiments of the invention, the treatment is by i.v. infusion once every eight weeks.

According to embodiments of the invention, the treatment is by i.v. infusion once every ten weeks.

According to embodiments of the invention, the treatment is by i.v. infusion once every twelve weeks.

According to embodiments of the invention, the recombinant homotetrameric uricase enzyme is formulated in a buffer comprising 10 mM sodium phosphate, 140 mM sodium chloride and 0.1 mM ethylenediaminetetraacetic acid (EDTA).

According to embodiments of the invention, the recombinant homotetrameric uricase enzyme is at a concentration of 2 mg/ml in the buffer.

According to embodiments of the invention, the recombinant homotetrameric uricase enzyme is a plant recombinant homotetrameric uricase enzyme.

According to embodiments of the invention, treating further comprises administering methotrexate to the subject.

According to embodiments of the invention, the disease or disorder is selected from the group consisting of gout, diabetes, kidney stones, tumor lysis syndrome, hemorrhagic shock, malaria, allergic inflammation, renal dysfunction, viral infection, acute gastroenteritis, placental inflammation, sterile inflammation, pregnancy complications, multiple sclerosis, inflammatory bowel disease, gastrointestinal infection, and Lesch-Nyhan syndrome.

According to embodiments of the invention, the disease or disorder is gout.

According to embodiments of the invention, the gout is severe gout or refractory gout.

According to embodiments of the invention, the subject has a serum urate level ≥4.5 mg/dL.

According to embodiments of the invention, the subject has a serum urate level ≥6 mg/dL.

According to embodiments of the invention, the subject has a serum urate level ≥7 mg/dL. According to embodiments of the invention, the gout is erosive gout or tophaceous gout.

According to embodiments of the invention, the subject has had more than two gout flares over the last year.

According to embodiments of the invention, the subject has persistent joint inflammation.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

DESCRIPTION OF SPECIFIC EMBODIMENTS OF THE INVENTION

The present invention, in some embodiments thereof, relates to therapy, and more particularly, but not exclusively, to novel forms of uricase and to uses thereof, for example, in reducing uric acid levels.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

WO2022/097141 discloses the recombinant homotetrameric uricase enzyme PRX-115 which comprises a substitution of cysteine (Cys) to lysine (Lys) at position 250 (prU-C250K). This molecule was shown to exhibit reduced and nearly nullified immunogenicity, and good stability in storage and in vivo.

The present inventors have now developed, through laborious experimentation and screening an effective novel therapeutic dose and regimen and formulation employing PRX-115 for the treatment of gout in human patients.

According to an aspect of some embodiments of the invention, there is provided a method of treating a disease or disorder associated with excessive uric acid levels in a subject in need thereof, comprising administering to the subject by i.v. infusion an amount of a recombinant homotetrameric uricase enzyme comprising four uricase polypeptides having the amino acid sequence as set forth in SEQ ID NO: 2, wherein the polypeptides are crosslinked by polyethylene glycol (PEG) bis-aldehyde having a molecular weight of 2-3.5 kDa, wherein the administering is no more than once every four weeks (i.e. a dose interval of more than 4 weeks), wherein the amount is selected from the group consisting of 1 mg per subject, 2.0 mg per subject, 3 mg per subject, 4.0 mg per subject, 8 mg per subject, 12 mg per subject, 16 mg per subject, 18 mg per subject 24 mg per subject, 36 mg per subject and 48 mg per subject.

In some embodiments, the recombinant uricase of the invention is administered according to the following dose regimen:

1.0 mg/person—once every 4 weeks, once every 6 weeks, once every 8 weeks, once every 10 weeks, once every 12 weeks;

2.0 mg/person—once every 4 weeks, once every 6 weeks, once every 8 weeks, once every 10 weeks, once every 12 weeks;

3.0 mg/person—once every 4 weeks, once every 6 weeks, once every 8 weeks, once every 10 weeks, once every 12 weeks;

4.0 mg/person—once every 4 weeks, once every 6 weeks, once every 8 weeks, once every 10 weeks, once every 12 weeks;

8.0 mg/person—once every 4 weeks, once every 6 weeks, once every 8 weeks, once every 10 weeks, once every 12 weeks;

12.0 mg/person—once every 4 weeks, once every 6 weeks, once every 8 weeks, once every 10 weeks, once every 12 weeks;

16.0 mg/person—once every 4 weeks, once every 6 weeks, once every 8 weeks, once every 10 weeks, once every 12 weeks;

18.0 mg/person—once every 4 weeks, once every 6 weeks, once every 8 weeks, once every 10 weeks, once every 12 weeks;

24.0 mg/person—once every 4 weeks, once every 6 weeks, once every 8 weeks, once every 10 weeks, once every 12 weeks;

36.0 mg/person—once every 4 weeks, once every 6 weeks, once every 8 weeks, once every 10 weeks, once every 12 weeks; or 48.0 mg/person—once every 4 weeks, once every 6 weeks, once every 8 weeks, once every 10 weeks, once every 12 weeks.

In other embodiments, the uricase is administered in the following dose regimens:

Low Dose (1.0 or 2.0 or 3.0 or 4.0 or 8.0 mg/person)—once every 4 weeks, once every 6 weeks, once every 8 weeks, once every 10 weeks, once every 12 weeks;

High Dose (8.0 or 12.0 or 16.0 or 18.0 or 24.0 or 48.0 mg/person)—once every 4 weeks, once every 6 weeks, once every 8 weeks, once every 10 weeks, once every 12 weeks;

In some embodiments, the uricase is administered along with methotrexate (MTX). In one embodiment, the uricase is administered in a high dose (8.0 or 12.0 or 16.0 or 18.0 or 24.0 or 48.0 mg/person) along with methotrexate (15 g/week) once every 4 weeks, once every 8 weeks or once every 12 weeks.

Herein, the term "uricase" encompasses any enzyme designated as EC 1.7.3.3 (catalyzing the oxidation of urate to 5-hydroxyurate, with concomitant conversion of $O_2$ to $H_2O_2$) or as EC 1.14.13.113 (catalyzing the oxidation of urate to 5-hydroxyurate, with concomitant oxidation of FADH and conversion of $O_2$ to $H_2O_2$); including both proteins with an amino acid sequence of a naturally occurring enzymes, as well as proteins with a homologous amino acid sequence (e.g., according to any of the embodiments described herein relating to homologs, as this term is defined herein).

In some of any of the embodiments described herein, the uricase is an EC 1.7.3.3 uricase.

The uricase polypeptide of this aspect of the present invention has the amino acid sequence as set forth in SEQ ID NO: 2. The enzyme comprises 4 polypeptides, each having the amino acid sequence as set forth in SEQ ID NO: 2.

The uricase polypeptide of any of the embodiments of the invention is purified (e.g., from plants or animal tissue) or generated by recombinant DNA technology. In some of any of the respective embodiments, the uricase polypeptide is a plant recombinant polypeptide; that is, generated by recombinant technology in a plant. *Nicotiana tabacum* (tobacco) is an exemplary plant for recombinant generation of a polypeptide.

A wide variety of techniques for recombinant generation of a polypeptide in various cells and/or organisms (including plants and plant cells) are known in the art.

A recombinant protein may optionally be characterized by post-translational modifications (e.g., glycosylation) characteristic of the type of cell and/or organism in which the recombinant protein is generated (e.g., a plant); as opposed, for example, the type of cell and/or organism which naturally expresses the polypeptide.

The term "plant" as used herein encompasses whole plants, a grafted plant, ancestors and progeny of the plants and plant parts, including seeds, shoots, stems, roots (including tubers), rootstock, scion, and plant cells, tissues and organs. The plant may be in any form including suspension cultures, embryos, meristematic regions, callus tissue, leaves, gametophytes, sporophytes, pollen, and microspores. Plants that are particularly useful in the methods of the invention include all plants which belong to the superfamily Viridiplantae, in particular monocotyledonous and dicotyledonous plants including a fodder or forage legume, ornamental plant, food crop, tree, or shrub such as *Acacia* spp., *Acer* spp., *Actinidia* spp., *Aesculus* spp., *Agathis australis, Albizia amara, Alsophila tricolor, Andropogon* spp., *Arachis* spp, *Areca catechu, Astelia fragrans, Astragalus cicer, Baikiaca plurijuga, Betula* spp., *Brassica* spp., *Bruguiera gymnorrhiza, Burkea africana, Butca frondosa, Cadaba farinosa, Calliandra* spp, *Camellia sinensis, Cannabaccac, Cannabis indica, Cannabis, Cannabis sativa*, Hemp, industrial Hemp, *Capsicum* spp., *Cassia* spp., *Centroema pubescens, Chacoomeles* spp., *Cinnamomum cassia, Coffea arabica, Colophospermum mopane, Coronillia varia, Cotoneaster serotina, Crataegus* spp., *Cucumis* spp., *Cupressus* spp., *Cyathea dealbata, Cydonia oblonga, Cryptomeria japonica, Cymbopogon* spp., *Cynthea dealbata, Cydonia oblonga, Dalbergia monetaria, Davallia divaricata, Desmodium* spp., *Dicksonia squarosa, Dibeteropogon amplectens, Dioclea* spp, *Dolichos* spp., *Dorycnium rectum, Echinochloa pyramidalis, Ehraffia* spp., *Eleusine coracana, Eragrestis* spp., *Erythrina* spp., *Eucalyptus* spp., *Euclea schimperi, Eulalia villosa, Pagopyrum* spp., *Feijoa sellowlana, Fragaria* spp., *Flemingia* spp, *Freycinetia banksli, Geranium thunbergii, Ginkgo biloba, Glycine javanica, Gliricidia* spp, *Gossypium hirsutum, Grevillea* spp., *Guibourtia coleosperma, Hedysarum* spp., *Hemaffhia altissima, Heteropogon contoffus, Hordeum vulgare, Hyparrhenia rufa, Hypericum erectum, Hypeffhelia dissolute, Indigo incamata, Iris* spp., *Leptarrhena pyrolifolia, Lespediza* spp., *Lettuca* spp., *Leucaena leucocephala, Loudetia simplex, Lotonus bainesli, Lotus* spp., *Macrotyloma axillare, Malus* spp., *Manihot esculenta, Medicago saliva, Metasequoia glyptostroboides, Musa sapientum, Nicotianum* spp., *Onobrychis* spp., *Ornithopus* spp., *Oryza* spp., *Peltophorum africanum, Pennisetum* spp., *Persea gratissima, Petunia spp., Phascolus* spp., *Phoenix canariensis, Phormium cookianum, Photinia* spp., *Picca glauca, Pinus* spp., *Pisum sativam, Podocarpus totara, Pogonarthria fleckii, Pogonaffhria squarrosa, Populus* spp., *Prosopis cineraria, Pseudotsuga menziesii, Pterolobium stellatum, Pyrus communis, Quercus* spp., *Rhaphiolepsis umbellata, Rhopalostylis sapida, Rhus natalensis, Ribes grossularia, Ribes* spp., *Robinia pseudoacacia, Rosa* spp., *Rubus* spp., *Salix* spp., *Schyzachyrium sanguineum, Sciadopitys vefficillata, Sequoia sempervirens, Sequoiadendron giganteum, Sorghum bicolor, Spinacia* spp., *Sporobolus fimbriatus, Stiburus alopecuroides, Stylosanthos humilis, Tadehagi* spp, *Taxodium distichum, Themeda triandra, Trifolium* spp., *Triticum* spp., *Tsuga heterophylla, Vaccinium* spp., *Vicia* spp., *Vitis vinifera, Watsonia pyramidata, Zantedeschia aethiopica, Zea mays*, amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash tea, and/or trees. Alternatively algae and other non-Viridiplantae can be used for the methods of some embodiments of the invention.

Alternatively, the polypeptides of some embodiments of the invention may be chemically synthesized by any techniques that are known to those skilled in the art of peptide synthesis. For solid phase peptide synthesis, a summary of the many techniques may be found in J. M. Stewart and J. D. Young, Solid Phase Peptide Synthesis, W. H. Freeman Co. (San Francisco), 1963 and J. Meienhofer, Hormonal Proteins and Peptides, vol. 2, p. 46, Academic Press (New York), 1973. For classical solution synthesis see G. Schroder and K. Lupke, The Peptides, vol. 1, Academic Press (New York), 1965.

In general, these methods comprise the sequential addition of one or more amino acids or suitably protected amino acids to a growing polypeptide chain. Normally, either the amino or carboxyl group of the first amino acid is protected by a suitable protecting group. The protected or derivatized amino acid can then either be attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final polypeptide compound. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide and so forth. Further description of peptide synthesis is disclosed in U.S. Pat. No. 6,472,505.

Large scale polypeptide synthesis is described by Andersson et al. [Biopolymers 2000; 55:227-250].

In some of any of the embodiments described herein, the homotetrameric uricase is characterized by a longer in vivo half-life than a corresponding non-modified uricase (i.e., without the linking moieties described herein). In some such embodiments described herein, the half-life of the modified uricase is at least 20% longer than that of the corresponding non-modified uricase. In some embodiments, the half-life of the modified uricase is at least 50% longer than that of the corresponding non-modified uricase. In some embodiments, the half-life of the modified uricase is at least 100% longer than—i.e., at least two-fold—that of the corresponding non-modified uricase. In some embodiments, the half-life of the modified uricase is at least three-fold that of the corresponding non-modified uricase. In some embodiments, the half-life of the modified uricase is at least five-fold that of the corresponding non-modified uricase. In some embodiments, the half-life of the modified uricase is at least 10-fold that of the corresponding non-modified uricase. In some embodiments, the half-life of the modified uricase is at least 20-fold that of the corresponding non-modified uricase. In some embodiments, the half-life of the modified uricase is at least 50-fold that of the corresponding non-modified uricase. In some embodiments, the half-life of the modified uricase is at least 100-fold that of the corresponding non-modified uricase.

A half-life of (modified and/or non-modified) uricase may be determined, for example, by determining an amount of the tested uricase in the blood (e.g., in plasma) over time, following injection of the tested uricase into a subject (e.g., in humans and/or in rats/dogs). As exemplified herein, an amount of uricase may be determined using an antibody against the tested uricase (e.g., by ELISA) and/or by determining an amount of enzymatic activity characteristic of uricase.

In some of any of the embodiments described herein, the modified uricase is characterized by a plasma half-life (e.g., as determined by antibody recognition and/or enzymatic activity) in rats of at least 40 hours. In some such embodiments, the half-life is at least 50 hours. In some embodiments, the half-life is at least 60 hours. In some embodiments, the half-life is at least 70 hours. In some embodiments, the half-life is at least 80 hours. In some embodiments, the half-life is at least 100 hours. In some embodiments, the half-life is at least one week, or at least two weeks, or at least three weeks, or at least four weeks.

A longer half-life of a modified uricase according to any of the respective embodiments described herein may optionally be associated with a greater molecular weight of the modified uricase (which may decrease a rate of removal from the bloodstream, e.g., by filtration in the kidneys) and/or by lower immunogenicity of the modified uricase (which may decrease a rate of inactivation and/or destruction by the immune system).

As used herein, the term "polyethylene glycol" describes a poly (alkylene glycol), wherein at least 50%, at least 70%, at least 90%, and preferably 100%, of the alkylene glycol units are —$CH_2CH_2$—O—. Similarly, the phrase "ethylene glycol units" is defined herein as units of —$CH_2CH_2O$.

Polyethylene glycol (PEG) bis-aldehyde (also referred to as bis-Ald-PEG) is a bifunctional PEG propionaldehyde.

Examples of suitable reducing agents include, without limitation, borane and complexes thereof (e.g., picoline borane complex), borohydrides (including borohydride salts, e.g., sodium borohydride), triacetoxyborohydrides (including triacctoxyborohydride salts, e.g., sodium triacetoxyborohydride), cyanoborohydrides (including cyanoborohydride salts, e.g., sodium cyanoborohydride), and any other reducing agent known in the art to be suitable for a reductive amination process. Exemplary reducing agents include, without limitation, a 2-picoline borane complex, and sodium cyanoborohydride.

The uricase polypeptide, crosslinking agent and reducing agent may optionally be combined in any order. For example, a crosslinking agent may optionally be added to a mixture comprising the polypeptide and reducing agent, or the polypeptide may optionally be added to a mixture comprising the crosslinking agent and reducing agent (e.g., such that a conjugate of the polypeptide and crosslinking agent is already in contact with the reducing agent upon formation of the conjugate). In some embodiments, the uricase polypeptide, crosslinking agent and reducing agent are combined essentially concomitantly (e.g., as a "one-pot reaction").

In some of any of the respective embodiments described herein, a molar ratio of the crosslinking agent to the uricase polypeptide contacted with the crosslinking agent is from 100:1 to 1,000:1.

According to a particular embodiment, the homotetrameric uricase enzyme is generated as follows: a solution of uricase polypeptides (having the amino acid sequence as set forth in SEQ ID NO: 2) are crosslinked using polyethylene glycol bis-aldehyde (bis-Ald-PEG) (e.g. 3.2 kDa) (e.g. commercially available from Creative PEGWorks) in phosphate buffer (pH 8). PEGylation and cross-linking are performed at excess of bis-aldehyde-PEG-3.4 kDa reagent at a weight ratio of approximately 24.9 gram reagent/1-gram prc-Uricase, corresponding to 1000 equivalent of PEG per protein. The chemical reaction is started by mixing the Sodium Phosphate buffer with bis-aldehyde-PEG-3.4 kD. Uricase polypeptides are added, followed by picolin borane, dissolved in Ethanol.

As mentioned, the recombinant homotetrameric uricase according to any of the respective embodiments described herein may optionally be for use in the treatment of a disease or disorder in which uricase activity is beneficial and/or for use in the treatment of a disease or disorder associated with excessive uric acid levels.

Uric acid levels can be measured in body fluids, including but not limited to urinary uric acid, serum uric acid or plasma uric acid. Measurement of uric acid in body fluids can be affected by assays including but not limited to colorimetric assays, biochemical assays, chromatographic assays and the like. In some embodiments, the plasma and/or serum uric acid is measured using an HPLC chromatographic assay.

Examples of conditions treatable according to some embodiments (according to any of the aspects described herein) include, without limitation, gout, diabetes, kidney stones, tumor lysis syndrome, hemorrhagic shock, malaria, allergic inflammation, renal dysfunction, viral infection, such as influenza and COVID-19 (e.g., wherein excessive uric acid levels are associated with an antiviral drug, such as favipiravir), acute gastroenteritis, placental inflammation, sterile inflammation and other pregnancy complications associated with uric acid (e.g., miscarriages, preeclampsia and preterm birth), multiple sclerosis, inflammatory bowel disease, gastrointestinal infection, and Lesch-Nyhan syndrome.

In some of any of the embodiments described herein, the treatment enhances dissolution of solid (e.g., crystalline) uric acid in the body, for example, in treating gout, kidney stones, placental inflammation, sterile inflammation, pregnancy complications, Lesch-Nyhan syndrome and/or tumor lysis syndrome.

In some of any of the embodiments described herein, the treatment reduces an inflammatory effect of uric acid, which may optionally be beneficial in treating an inflammatory condition, for example, gout, malaria, allergic inflammation, viral infection (e.g., COVID-19), acute gastroenteritis, placental inflammation, sterile inflammation, pregnancy complications, multiple sclerosis, and inflammatory bowel disease.

According to a particular embodiment, the disease which is being treated is gout. In one embodiment, the gout is severe gout. In another embodiment, the gout is refractory gout.

In one embodiment, the subject being treated for gout has a serum urate level ≥4-6 mg/dL.

In some embodiments, the subject being treated for gout has a serum urate level ≥4.7 mg/dL.

In some embodiments, the subject being treated for gout has a serum urate level ≥6 mg/dL.

In addition, the subject may present with at least one of the following symptoms:

1. The subject shows symptoms of erosive gout (as measured by clinical state, presence of at least one joint erosion);
2. The subject show symptoms of tophaceous gout (as measured by clinical state, presence of at least one subcutaneous tophus);
3. The subject presents with recurrent gout flares (for example had had at least two or more in twelve months); and/or
4. The subject presents with persistent joint inflammation. This may be manifested by a limitation of range of motion with presence of MSU crystals not attributable clinically to other causes.

In one embodiment, the subject being treated for gout has a serum urate level ≥7 mg/dL.

Additionally, the subject may show at least one of the following symptoms:

1. symptoms of erosive gout (as measured by clinical state, presence of at least one joint erosion);
2. symptoms of tophaceous gout (as measured by clinical state, presence of at least one subcutaneous tophus);
3. presents with recurrent gout flares (for example had had at least two or more in six months or three or more in twelve months); and/or
4. The subject presents with persistent joint inflammation. This may be manifested by a limitation of range of motion with presence of MSU crystals not attributable clinically to other causes.

According to another embodiment, the subject being treated for gout has a serum urate level ≥8 mg/dL.

Additionally, the subject may show at least one of the following symptoms:

1. symptoms of erosive gout;

recurrent gout flares (three or more flares in eighteen months or two or more flares in 12 months);

2. the subject presents with at least one tophi; and/or
3. the subject presents with gout arthropathy (joint damage to the gout as diagnosed clinically or radiographically).

According to a particular embodiment, the subject being treated for gout does not have arthritis, or any condition known to have arthritis as a clinical manifestation, including but not limited to rheumatoid arthritis, psoriatic arthritis, ankylosing and non-radiographic spondylitis, reactive arthritis, psoriasis, inflammatory bowel diseases, chondrocalcinosis, or pyrophosphate arthritis.

In another embodiment, the subject being treated for gout may have osteoarthritis.

In another embodiment, the subject being treated for gout does not have diabetes (e.g. uncontrolled diabetes, or is not being treated with insulin).

In some embodiments, the subject being treated for gout is between 18 and 80 years old. In other embodiments, the subject being treated for gout is between 18 and 65 years old.

The recombinant uricase according to any of the respective embodiments described herein may optionally be used per se, or alternatively, as part of a pharmaceutical composition which further comprises a pharmaceutically acceptable carrier.

Treatment with the recombinant uricase according to any of the respective embodiments may provide improvement in any of a number of metrics which can be evaluated over the course of treatment, for documentation as well as for monitoring of the subject being treated for gout (e.g., in order to adjust dosage, dose regimen, adjunct therapies and the like).

In some embodiments, the clinical metrics which can be evaluated priori to, during and/or following treatment with the recombinant uricase of the invention include, but are not limited to:

Uric Acid

Concentration (e.g. plasma UA) concentration over time of pUA

Tophi

Change from baseline of at least one tophus longest diameter

Flares

Number of gout flares over time

Swollen Joints

Change in Number of Swollen Joints over time

Tender Joints

Change in Number of Tender Joints over time

Quality of life;

Change in patient reported outcomes as assessed by commonly accepted scales, including but not limited to:

Health Assessment Questionnaire (HAQ: VAS pain scale)

HAQ disability index (HAQ-DI)

SF-36 Physical Component Summary Score (SF36-PCS (including Mental Assessment)).

Comorbidities

Change in blood pressure

Change in hepatic fibrosis (e.g. estimated by Fibrosis-4 index)

Acute medications

Change in the use of analgesic acute drugs for treatment of pain due to gout flares over time.

Further, other clinical metrics can be incorporated into the monitoring of the subject being treated for gout with the recombinant uricase of the invention, such as (but not limited to):

Change in the clinical laboratory tests (serum chemistry, lipids, hematology, and urinalysis)

Change in vital signs (pulse, respiratory rate, systolic and diastolic blood pressure, and body temperature measurements)

Clinically significant changes in physical examination, including body weight

Standard 12-lead electrocardiogram (ECG) findings

Occurrence of hypersensitivity/anaphylaxis reactions using standardized criteria Change in concomitant medication In some embodiments, treatment with the recombinant uricase of the invention results in improvement in at least one of the abovementioned clinical metrics. In one embodiment, treatment of the subject being treated for gout with the recombinant uricase of the invention provides improvement in at least one of the clinical metrics, greater than the improvement in the same or similar metrics measured for subjects being treated for gout with compositions or methods other than the recombinant uricase of the invention.

As used herein a "pharmaceutical composition" refers to a preparation of one or more species of modified uricase described herein, with other chemical components such as pharmaceutically acceptable and suitable carriers and excipients. The purpose of a pharmaceutical composition is to facilitate administration of a compound to an organism.

Hereinafter, the term "pharmaceutically acceptable carrier" refers to a carrier or a diluent that does not cause significant irritation to an organism and does not abrogate the biological activity and properties of the administered compound. Examples, without limitations, of carriers are: propylene glycol, saline, emulsions and mixtures of organic solvents with water, as well as solid (e.g., powdered) and gaseous carriers.

Techniques for formulation and administration of drugs may be found in "Remington's Pharmaceutical Sciences" Mack Publishing Co., Easton, PA, latest edition, which is incorporated herein by reference.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more pharmaceutically acceptable carriers comprising excipients and auxiliaries, which facilitate processing of the modified uricase into preparations which can be used pharmaceutically. Proper formulation is dependent upon the route of administration chosen.

The modified uricase described herein may be formulated for parenteral administration, e.g., by bolus injection or continuous infusion. Formulations for injection or infusion may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the modified uricase preparation in water-soluble form. For injection or infusion, the modified uricase may optionally be formulated in aqueous solutions, preferably in physiologically compatible buffers such as Hank's solution, Ringer's solution, or physiological saline buffer with or without organic solvents such as propylene glycol, polyethylene glycol.

An exemplary carrier contemplated by the present inventors includes 10 mM sodium phosphate, 140 mM sodium chloride and 0.1 mM ethylenediaminetetraacetic acid (EDTA).

The recombinant uricase may be solubilized in the carrier at a concentration of 1 mg/ml-5 mg/ml. In one embodiment, the recombinant uricase is solubilized in the carrier at a concentration of 2 mg/ml. Typically, the intravenous infusion takes between 0.5 and 4 hours, for example 3 hours. In some embodiments, the infusion takes an hour, 1.5 hours, 2 hours or 2.5 hours.

Pharmaceutical compositions suitable for use in the context of the present invention include compositions wherein the active ingredients are contained in an amount effective to achieve the intended purpose. More specifically, a therapeutically effective amount means an amount of modified uricase effective to prevent, alleviate or ameliorate symptoms of disease or prolong the survival of the subject being treated.

For any modified uricase used in the methods of the invention, the therapeutically effective amount or dose can be estimated initially from activity assays in animals. For example, a dose can be formulated in animal models to achieve a circulating concentration range that includes the $IC_{50}$ as determined by activity assays (e.g., the concentration of the test protein structures, which achieves a half-maximal increase in a biological activity of the modified uricase). Such information can be used to more accurately determine useful doses in humans.

Following administration, the present inventors further contemplate analyzing the level of uric acid in the subject, check the number of flares, the use of analgesic drugs, tenderness of the joints, quality of life of the subject. On the basis of these parameters the dose may be adjusted accordingly.

Toxicity and therapeutic efficacy of the modified uricase described herein can be determined by standard pharmaceutical procedures in experimental animals, e.g., by determining the $EC_{50}$, the $IC_{50}$ and the $LD_{50}$ (lethal dose causing death in 50% of the tested animals) for a subject protein structure. The data obtained from these activity assays and animal studies can be used in formulating a range of dosage for use in human.

In some embodiments, premedication is provided prior to the administration of the modified uricase, in order to minimize the risk of infusion-related reactions. In some embodiments, the premedication comprises antihistamines and/or corticosteroids. In one embodiment, premedication comprises oral antihistamines loratadine (10 mg) and famotidine (40 mg) and the corticosteroid prednisone (50 mg), administered orally 12 hours and 2 hours prior to the infusion.

The dosage may vary depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1 p. 1).

Dosage amount and interval may be adjusted individually to provide plasma levels of the active uricase which are sufficient to maintain the desired effects, termed the minimal effective concentration (MEC). The MEC will vary for each preparation, but can be estimated from in vitro data; e.g., the concentration necessary to achieve the desired level of activity in vitro. Dosages necessary to achieve the MEC will depend on individual characteristics and route of administration. HPLC assays or bioassays can be used to determine plasma concentrations.

Dosage intervals can also be determined using the MEC value. Preparations should be administered using a regimen, which maintains plasma levels above the MEC for 10-90% of the time, preferable between 30-90% and most preferably 50-90%.

In some of any of the embodiments described herein, administration (e.g., by i.v. infusion) is effected at an interval of about at least fours weeks, optionally at intervals of about four weeks, about six weeks, about eight weeks, about 10 weeks or about 12 weeks.

Thus, for example, the following doses are contemplated when administered once every four weeks: about 1 mg per subject, about 2.0 mg per subject, about 3 mg per subject, about 4.0 mg per subject, about 8 mg per subject, about 12 mg per subject, about 16 mg per subject, about 18 mg per subject, about 24 mg per subject, about 36 mg per subject and about 48 mg per subject. Preferably, the doses are about 3 mg per subject, about 8 mg per subject, about 36 mg per subject or about 48 mg per subject. Typically, the dose amounts are suitable for subjects of any weight (e.g. between 45 kg-120 Kg, more preferably between 60-100 kg). The dose amounts may also be calculated per BMI. In one instance the dose amounts is suitable for subjects having a BMI between 18.5 to 50. However, it will be appreciated that the present inventors also contemplate adjusting the dose according to the weight or BMI of the subject, by estimating that the amounts provided herein are suitable for a human of average weight—70 kg, or a BMI of 33.

Thus, for example, the following doses are contemplated when administered once every six weeks: 1 mg per subject, about 2.0 mg per subject, about 3 mg per subject, about 4.0 mg per subject, about 8 mg per subject, about 12 mg per subject, about 16 mg per subject, about 18 mg per subject, about 24 mg per subject, about 36 mg per subject and about 48 mg per subject. Preferably, the doses are about 1 mg per subject, about 2.0 mg per subject, about 4 mg per subject, about 16 mg per subject, about 24 mg per subject and about 48 mg per subject.

Thus, for example, the following doses are contemplated when administered once every eight weeks: 1 mg per subject, about 2.0 mg per subject, about 3 mg per subject, about 4.0 mg per subject, about 8 mg per subject, about 12 mg per subject, about 16 mg per subject, about 18 mg per subject, about 24 mg per subject, about 36 mg per subject and about 48 mg per subject. Preferably, the doses are about 1 mg per subject, about 2.0 mg per subject, about 3 mg per subject, about 18 mg per subject, about 24 mg per subject and about 36 mg per subject.

Thus, for example, the following doses are contemplated when administered once every ten weeks: about 1 mg per subject, about 2.0 mg per subject, about 3 mg per subject, about 4.0 mg per subject, about 8 mg per subject, about 12 mg per subject, about 16 mg per subject, about 18 mg per subject, about 24 mg per subject, about 36 mg per subject or about 48 mg per subject.

Thus, for example, the following doses are contemplated when administered once every twelve weeks: about 1 mg per subject, about 2.0 mg per subject, about 3 mg per subject, about 4.0 mg per subject, about 8 mg per subject, about 12 mg per subject, about 16 mg per subject, about 18 mg per subject, about 24 mg per subject, about 36 mg per subject or about 48 mg per subject.

Additional doses contemplated by the present invention include:

24 mg per month, 48 mg once every two months, 16 mg once a month, 18 mg once every two months, 24 mg once every two months, 8 mg per month, 12 mg once every two months, 16 mg once every two months, 8 mg once every two months, 1 mg per month, 16 mg once every three months, 18 mg once every three months, 36 mg once every two months, 8 mg once every three months and 12 mg once every three months.

Compositions of the present invention may, if desired, be presented in a pack or dispenser device, such as an FDA (the U.S. Food and Drug Administration) approved kit, which may contain one or more unit dosage forms containing the active ingredient. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising a modified uricase of any of the embodiments of the invention formulated in a compatible pharmaceutical carrier may also be prepared, placed in an appropriate container, and labeled for treatment of an indicated condition or diagnosis, as is detailed herein.

Thus, according to an embodiment of the present invention, the pharmaceutical composition described herein is packaged in a packaging material and identified in print, in or on the packaging material, for use in the treatment of a condition in which the activity of the modified uricase is beneficial, as described hereinabove.

As used herein the term "about" refers to +10% or +5%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Example I: Clinical Trial Testing PRX-115 for the Treatment of Gout

Active Agent:

PRX-115 is a recombinant homotetrameric uricase enzyme from *Candida utillis* with substitution of cystein (Cys) to lysin (Lys) at position 250 (prU-C250K), which is expressed in *Nicotiana tabacum* (tobacco) cells. The mature uricase monomer (known as the prU-C250K intermediate)

contains 303 amino acids with no potential N-linked glycosylation sites giving a calculated weight of 34069 Da. The prU-C250K intermediate undergoes post purification modification with unique bi-functional aldehyde (Ald) PEG units, each of which has an average weight of 3400 Da (bis-Ald-3400 PEG) resulting with a PEGylated homotetramer, referred as PRX-115.

PRX-115 is formulated in an aqueous solution buffer comprised of 10 mM sodium phosphate, 140 mM sodium chloride and 0.1 mM ethylenediaminetetraacetic acid (EDTA). PEG occupancy is approximately 42 PEGs per enzyme unit and the calculated molecular weight (MW) (including PEG) is approximately 275 kDa (range of 271793-283645 Da depending on the numbers of PEGs).

Dose Regimen:

PRX-115 or placebo will be provided as a single dose by intravenous (IV) infusion over 3.0 hours (±15 minutes).

The following dose regimens will be tested, in single doses:

1.0 mg/person;
2.0 mg/person;
3.0 mg/person;
4.0 mg/person;
8.0 mg/person;
12.0 mg/person;
16.0 mg/person;
18.0 mg/person;
24.0 mg/person;
36.0 mg/person;
48.0 mg/person;

Participant Inclusion Criteria:

Males or females 18 to 65 years of age, inclusive.

Serum uric acid >4.8.0 mg/dL (0.35 mmol/L) at the Screening visit.

Body mass index within the range 18.5 to 50 kg/m$^2$, inclusive, at the Screening visit.

Participant Exclusion Criteria:

1. Has any condition known to have arthritis as a clinical manifestation: rheumatoid arthritis, psoriatic arthritis, ankylosing and non-radiographic spondylitis, reactive arthritis, psoriasis, inflammatory bowel diseases, chondrocalcinosis, or pyrophosphate arthritis.
2. Infectious disease:

Clinically significant acute systemic infection and/or antibiotic treatment within 28 days prior to the Screening visit.

Any chronic infection that was symptomatic within 3 months prior to Screening, not including fungal foot infection.

Known history of, or a positive test result for, hepatitis B surface antigen (HBsAg), hepatitis C virus antibodies (HCV Ab), human immunodeficiency virus (HIV) Type 1 or Type 2 Ab (according to 4$^{th}$ generation serology testing).

3. Major trauma or major surgery in the 6 months before Screening or at any time between Screening and the dose of IP, or major surgery scheduled during the study.
4. History of malignancy or treatment of malignancy in the last 5 years, excluding non-melanoma skin carcinoma, or localized carcinoma in situ of the cervix.
5. Had ≥1 gout flare in the last year prior to either Screening or Day −1.
6. Has clinical evidence of subcutaneous tophi at either Screening or Day −1.
7. Estimated glomerular filtration rate (eGFR) value ≤60 mL/min/1.73 m$^2$ using Chronic Kidney Disease Epidemiology Collaboration (CKD-EPI) equation at either Screening and/or Day −1.
8. Average QT interval corrected using Fridericia's formula (QTcF) >450 ms for male participants or >470 ms for female participants, or any other abnormal ECG findings that are considered by the Investigator to be clinically significant, at either Screening or Day −1.
9. History of significant renal disease, and/or presence of renal stones at either Screening or Day −1.
10. The participant has a known allergy or sensitivity to the injected proteins, including pegylated products, or any other component of the formulation. In addition, presence of history of allergies requiring acute or chronic treatment (except for seasonal allergic like rhinitis, and at the discretion of the Investigator).
11. Has a history of anaphylaxis, severe allergic reactions, or severe atopy.
12. History of significant hematological disorders within the previous 5 years.
13. History of autoimmune disorders, and/or participant is immunocompromised or treated with immunosuppressive medications.
14. Has evidence of cardiovascular or cerebrovascular disease. This includes participants who have had any prior cardiac/vascular event(s) including myocardial infarction, unstable angina, stroke, transient ischemic attack or any revascularization procedure, clinically significant arrhythmia, or participants who are deemed, by their physician or PI, to have active cardiovascular, cerebrovascular, or peripheral vascular symptoms/disease.
15. History of congestive heart failure, New York Heart Association Class III or IV.
16. Seated/semi-recumbent BP outside the range of 90 to 150 mm Hg for systolic or 50 to 95 mm Hg for diastolic (following at least a 5-minute rest) at either Screening or Day −1.

Participants with hypertension who are not on stable medication for at least 6 months.

17. Seated/semi-recumbent heart rate outside the range of 45 to 100 beats/minute at either Screening or Day −1.
18. Tympanic temperature outside the interval of 35.5 to 37.5° C. at either Screening or Day −1.
19. Clinical laboratory test abnormalities as listed below:

a. Clinical laboratory values with Common Terminology Criteria for Adverse Events (CTCAE version 5.0) at Grade 2 or above b. Lactate dehydrogenase (LDH) ≥3× upper limit of normal (ULN)

c. Eosinophils ≥10% or >500 cells/uL, and deemed clinically significant d. Urinalysis with any clinically significant finding c. Alanine aminotransferase (ALT) and aspartate aminotransferase (AST) ≥3×ULN at Screening Laboratory samples taken in fasting conditions have total blood glucose >180 mg/dL (equivalent to 10 mmol/L). Note: participants with diabetes mellitus should be on stable medications for 2 months prior to screening. However, participants treated with insulin should be excluded.

20. Has uncontrolled type 2 diabetes at Screening with HbA1c ≥8.0% (≥64 mmol/mol). Participants with type 1 diabetes are excluded.
21. Concurrent treatment with urate lowering drugs (ULDs), such as allopurinol, febuxostat, probenecid, benzbromarone, benziodarone, sulphinpyrazone and lesinurad. Concurrent treatment with other medications known to influence uric acid metabolism or clearance will also be exclusionary, except for use of the following medications at stable doses for at least 2 months prior to Screening: diuretics, atorvastatin, fenofibrate, acetyl-salicylic acid, inhibitors of the sodium-glucose cotransporter-2.

22. Prior exposure to any experimental or marketed uricase (eg, rasburicase [Elitek, Fasturtec], pegloticase [Krystexxa®], pegadricase [SEL-212]).

23. Glucose-6-phosphate dehydrogenase (G6PD) deficiency or known catalase deficiency.

Example II: A Multicenter, Randomized, Double-Blind, Placebo-Controlled Study Assessing the Efficacy, Safety, and Tolerability of Multiple Intravenous Infusions of PRX-115 with or without Methotrexate Versus Placebo in Adult Patients with Chronic Gout Active Agent:

PRX-115 is a recombinant homotetrameric uricase enzyme from *Candida utillis* with substitution of cystein (Cys) to lysin (Lys) at position 250 (prU-C250K), which is expressed in *Nicotiana tabacum* (tobacco) cells. The mature uricase monomer (known as the prU-C250K intermediate) contains 303 amino acids with no potential N-linked glycosylation sites giving a calculated weight of 34069 Da. The prU-C250K intermediate undergoes post purification modification with unique bi-functional aldehyde (Ald) PEG units, each of which has an average weight of 3400 Da (bis-Ald-3400 PEG) resulting with a PEGylated homotetramer, referred as PRX-115.

PRX-115 is formulated in an aqueous solution buffer comprised of 10 mM sodium phosphate, 140 mM sodium chloride and 0.1 mM ethylenediaminetetraacetic acid (EDTA). PEG occupancy is approximately 42 PEGs per enzyme unit and the calculated molecular weight (MW) (including PEG) is approximately 275 kDa (range of 271793-283645 Da depending on the numbers of PEGs).

In some cohorts, PRX-115 is administered with methotrexate.

Dose Regimen:

PRX-115 or placebo is provided by intravenous (IV) infusion over 0.5-3.0 hours (+15 minutes).

The following dose regimens are tested:

Low Dose (1.0 or 2.0 or 3.0 or 4.0 or 8.0 mg/person)—once every 4 weeks, once every 8 weeks, once every 12 weeks;

High Dose (8.0 or 12.0 or 16.0 or 18.0 or 24.0 or 48.0 mg/person)—once every 4 weeks, once every 8 weeks, once every 12 weeks;

High Dose (8.0 or 12.0 or 16.0 or 18.0 or 24.0 or 48.0 mg/person) and Methotrexate (15 g/week) once every 8 weeks.

Premedication

Loratadine 10 mg, Famotidine 40 mg and Prednisone 50 mg, administered orally 12 and 2 hours prior to the start of the infusion.

Participant Inclusion Criteria:

Males or females 18 to 80 years of age, inclusive.

Serum uric acid >7.0 mg/dL (0.41 mmol/L) at the Screening visit.

Body mass index within the range 18.5 to 50 kg/m$^2$, inclusive, at the Screening visit.

Hyperuricemia: sUA over the saturation threshold sUA (≥7 mg/dL)

One of the following of severe gout:

Tophaceous gout (clinical state, presence of at least one subcutaneous tophus)

Recurrent gout flares (≥2 in 12 months)

Erosive gout (clinical state, presence of at least one joint erosion)

As evidence by either clinical signs consistent with chronic synovitis on clinical examination or the presence of typical gouty erosion(s) on hand and/or foot Participant Exclusion Criteria:

1. Has any condition known to have arthritis as a clinical manifestation: rheumatoid arthritis, psoriatic arthritis, ankylosing and non-radiographic spondylitis, reactive arthritis, psoriasis, inflammatory bowel diseases, chondrocalcinosis, or pyrophosphate arthritis (osteoarthritis is not an exclusion criterion).
2. Infectious disease:

Clinically significant acute systemic infection and/or antibiotic treatment within 28 days prior to the first visit.

Any chronic infection.

Known history of, or a positive test result for, hepatitis B surface antigen (HBsAg), hepatitis C virus antibodies (HCV Ab), human immunodeficiency virus (HIV) Type 1 or Type 2 Ab (according to 4$^{th}$ generation serology testing).

3. Major trauma or major surgery in the 6 months before Screening or at any time between Screening and the dose of IMP, or major surgery scheduled during the study.
4. History of malignancy or treatment of malignancy in the last 5 years, excluding localized, non-melanoma skin cancers (basal cell, squamous cell).
5. Pregnant or lactating woman or plans to be pregnant during the study.
6. The participant has a known allergy or sensitivity to the injected proteins, including pegylated products, or any other component of the formulation. In addition, presence of history of allergies requiring acute or chronic treatment (except for seasonal allergic like rhinitis, and at the discretion of the Investigator).
7. Has a history of anaphylaxis, severe allergic reactions, or severe atopy.
8. History of significant hematological disorders within the previous 5 years.
9. History of autoimmune disorders, and/or participant is immunocompromised or treated with immunosuppressive medications.
10. Donated or received any blood or blood products (eg, white blood cells, platelets, etc) within the 60 days prior to screening, or has donated blood or blood products on 2 or more occasions within the 6 months prior IMP administration, or the subject has donated plasma within 7 days before the screening visit, or has planned donations during the 84 days or 5 half-lives following IMP administration, whichever is longer.
11. Has evidence of unstable cardiovascular or cerebrovascular disease. This includes participants who have had any prior cardiac/vascular event(s) including myocardial infarction, unstable angina, stroke, transient ischemic attack or any revascularization procedure, clinically significant arrhythmia, or participants who are deemed, by their physician or PI, to have active cardiovascular, cerebrovascular, or peripheral vascular symptoms/disease.
12. History of congestive heart failure, New York Heart Association Class III or IV.

13. Clinically significant abnormalities on the ElectroCardioGram (ECG).
14. Is receiving ongoing pharmacological or non-pharmacological treatment for arrhythmia, including AICD.
15. Uncontrolled seated/semi-recumbent BP defined as >140/90 mmHg following at least 5-minutes of rest.
16. Orthostatic hypotension defined as a reduction in standing systolic BP by >20 mmHg from the average systolic BP in the seated or semi-recumbent position.
17. Body temperature outside 35.5 to 37.5° C. on screening.
18. Clinical laboratory test abnormalities as listed below:
    - Lactate dehydrogenase (LDH) ≥3× upper limit of normal (ULN)
    - Eosinophils ≥10% or >500 cells/uL, and deemed clinically significant
    - Urinalysis with any clinically significant finding including urine albumin creatinine ratio (UACR) >30 mg/g
    - Estimated Glomerular Filtration Rate (eGFR) ≤40 mL/min/1.73 $m^2$ (due to colchicine clearance)
    - White blood cell count (WBC) <$3.0\times10^9$/L
    - Serum aspartate aminotransferase (AST) or alanine amino transferase (ALT) >3× upper limit of normal (ULN) in the absence of known active liver disease
    - Hemoglobin (Hgb) <9 g/dL
19. Has uncontrolled type 2 diabetes at Screening with HbA1c ≥8.0% (≥64 mmol/mol) and/or fasting glucose >180 mg/dL. Participants with type 1 diabetes are excluded.
20. Participated in a clinical study with an investigational drug (small molecule within 30 days or large molecule within 180 days prior to the first dose of IMP.
21. Concurrent treatment with urate lowering drugs (ULDs), such as allopurinol, febuxostat, probenecid, benzbromarone, benziodarone, sulphinpyrazone and lesinurad.
22. Prior exposure to any experimental or marketed uricase (eg, rasburicase [Elitek, Fasturtec], pegloticase [Krystexxa®], pegadricase [SEL-212]).
23. Subject treated with medication which are known to have influence on uric acid metabolism or clearance.
24. Glucose-6-phosphate dehydrogenase (G6PD) deficiency or known catalase deficiency.
25. Intolerance and/or known contraindication to all protocol standard gout flare prophylaxis regimens.
26. Current or chronic treatment with systemic immunosuppressive agents such as MTX, azathioprine, or mycophenolate mofetil; prednisone ≥10 mg/day or equivalent dose of other corticosteroid on a chronic basis.
27. A known intolerance and/or known contraindication to MTX treatment or MTX treatment considered inappropriate.
28. History of hypoxanthine-guanine phosphoribosyltransferase deficiency, such as Lesch-Nyhan and Kelley-Seegmiller syndrome.
29. Has uncontrolled type 2 diabetes at Screening with HbA1c ≥8.0% (≥64 mmol/mol). Participants with type 1 diabetes are excluded.
30. Immunocompromised state, regardless of etiology.
31. Has received live vaccine (except influenze and COVID-19) in 3 months prior to visit.
32. Has history of moderate or severe alcohol or substance abuse within 12 months of study.
33. Positive alcohol or drug test at Screening.

32. Subject cannot participate or successfully complete the study, in the opinion of the investigator.

Study End Points:

Safety and Tolerability:
- Change in the clinical laboratory tests (serum chemistry, lipids, hematology, and urinalysis)
- Change in vital signs (pulse, respiratory rate, systolic and diastolic blood pressure, and body temperature measurements)
- Clinically significant changes in physical examination, including body weight
- Abnormal standard 12-lead electrocardiogram (ECG) findings
- Occurrence of hypersensitivity/anaphylaxis reactions using standardized criteria
- Change in concomitant medication
- Number (%) of patients who did not complete the treatment due to adverse events
- To evaluate the immunogenicity of PRX-115; Immunogenicity measure, i.e., the anti-drug antibodies (ADA) incidence and characteristics (eg, onset, duration, e.g., titer and specificity) over study treatment period and follow-up.
- IgE and C3/C4 complement assessments following any severe hypersensitivity reaction Efficacy Measures:
- Uric Acid
- Area under the Concentration (pUA) Curve (AUC; concentration over time) of pUA at weeks 9, 10, 11, 12 and 13 and/or month 6 (weeks 21, 22, 23, 24 and 25)
- Tophi
- Change from baseline of one tophus longest diameter (for those that have tophus at baseline) at month 6 as assessed by using Vernier digital caliper
- Flares
- Number (%) of subjects with at least one gout flare over 3-month period; months 1-3 and months 4-6
- Swollen Joints
- Change in Number of Swollen Joints from Baseline to Month 6
- Tender Joints
- Change in Number of Tender Joints from baseline to Month 6
- Quality of life;
- Change in patient reported outcomes from Baseline to Month 6 as assessed by
- Health Assessment Questionnaire (HAQ: VAS pain scale)
- HAQ disability index (HAQ-DI)
- SF-36 Physical Component Summary Score (SF36-PCS (including Mental Assessment)).
- Comorbidities
- Change from Baseline to Month 3 and/or 6 in blood pressure
- Change from Baseline to Month 6 in hepatic fibrosis estimated by Fibrosis-4 index
- Acute medications
- The use of analgesic acute drugs for treatment of pain due to gout flares during month 6.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

SEQUENCE LISTING

```
Sequence total quantity: 2
SEQ ID NO: 1            moltype = AA  length = 303
FEATURE                 Location/Qualifiers
source                  1..303
                        mol_type = protein
                        organism = Candida utilis
SEQUENCE: 1
MSTTLSSSTY GKDNVKFLKV KKDPQNPKKQ EVMEATVTCL LEGGFDTSYT EADNSSIVPT  60
DTVKNTILVL AKTTEIWPIE RFAAKLATHF VEKYSHVSGV SVKIVQDRWV KYAVDGKPHD  120
HSFIHEGGEK RITDLYYKRS GDYKLSSAIK DLTVLKSTGS MFYGYNKCDF TTLQPTTDRI  180
LSTDVDATWV WDNKKIGSVY DIAKAADKGI FDNVYNQARE ITLTTFALEN SPSVQATMFN  240
MATQILEKAC SVYSVSYALP NKHYFLIDLK WKGLENDNEL FYPSPHPNGL IKCTVVRKEK  300
TKL                                                                 303

SEQ ID NO: 2            moltype = AA  length = 303
FEATURE                 Location/Qualifiers
REGION                  1..303
                        note = C250K point mutation of SEQ ID NO: 1
source                  1..303
                        mol_type = protein
                        organism = synthetic construct
SEQUENCE: 2
MSTTLSSSTY GKDNVKFLKV KKDPQNPKKQ EVMEATVTCL LEGGFDTSYT EADNSSIVPT  60
DTVKNTILVL AKTTEIWPIE RFAAKLATHF VEKYSHVSGV SVKIVQDRWV KYAVDGKPHD  120
HSFIHEGGEK RITDLYYKRS GDYKLSSAIK DLTVLKSTGS MFYGYNKCDF TTLQPTTDRI  180
LSTDVDATWV WDNKKIGSVY DIAKAADKGI FDNVYNQARE ITLTTFALEN SPSVQATMFN  240
MATQILEKAK SVYSVSYALP NKHYFLIDLK WKGLENDNEL FYPSPHPNGL IKCTVVRKEK  300
TKL                                                                 303
```

What is claimed is:

1. A method of treating gout in a subject in need thereof, comprising administering to the subject by i.v. infusion an amount of a recombinant homotetrameric uricase enzyme comprising four uricase polypeptides having the amino acid sequence as set forth in SEQ ID NO: 2, wherein said polypeptides are crosslinked by polyethylene glycol (PEG) bis-aldehyde having a molecular weight of 2-3.5 kDa, wherein said administering is no more than once every four weeks, wherein said amount is 36 mg per subject.

2. The method of claim 1, wherein said polypeptides are crosslinked by polyethylene glycol (PEG) bis-aldehyde having a molecular weight of 3.5 kDa.

3. The method of claim 1, wherein said administering is effected over a period of about 1 hour, or about 1.5 hours, or about 2 hours or about 3 hours.

4. The method of claim 1, wherein said administering is effected once every four weeks.

5. The method of claim 1, wherein said administering is effected once every six weeks.

6. The method of claim 1, wherein said administering is effected once every eight weeks.

7. The method of claim 1, wherein said administering is effected once every ten weeks.

8. The method of claim 1, wherein said administering is effected once every twelve weeks.

9. The method of claim 1, wherein:

i) said recombinant homotetrameric uricase enzyme is formulated in a buffer comprising 10 mM sodium phosphate, 140 mM sodium chloride and 0.1 mM ethylenediaminetetraacetic acid (EDTA), and/or ii) said recombinant homotetrameric uricase enzyme is at a concentration of 2 mg/ml in said buffer, and/or iii) said recombinant homotetrameric uricase enzyme is a plant recombinant homotetrameric uricase enzyme.

10. The method of claim 1, wherein said treating further comprises administration of methotrexate to said subject.

11. The method of claim 1, wherein:

i) said gout is severe gout or refractory gout, and/or ii) the gout is erosive gout or tophaceous gout.

12. The method of claim 1, wherein:

i) the subject has a serum urate level ≥6 mg/dL, or ii) the subject has a serum urate level ≥7 mg/dL.

13. The method of claim 1, wherein:

i) the subject has had more than two gout flares over the last year, and/or ii) the subject has persistent joint inflammation.

* * * * *